United States Patent [19]

Ohfune et al.

[11] Patent Number: 5,068,412
[45] Date of Patent: Nov. 26, 1991

[54] (2R,3S,4S)-α-(CARBOXYCYCLOPROPYL)GLYCINE

[75] Inventors: Yasufumi Ohfune; Keiko Shimamoto, both of Osaka; Haruhiko Shinozaki; Michiko Ishida, both of Saitama, all of Japan

[73] Assignee: Suntory Limited, Osaka, Japan

[21] Appl. No.: 422,796

[22] Filed: Oct. 17, 1989

[30] Foreign Application Priority Data

Oct. 17, 1988 [JP] Japan ................................ 63-261155

[51] Int. Cl.$^5$ ............................................ C07C 101/20
[52] U.S. Cl. .................................................... 562/506
[58] Field of Search .......................................... 562/506

[56] References Cited

U.S. PATENT DOCUMENTS 4,959,493 9/1990 Ohfune ................................ 562/506

OTHER PUBLICATIONS

Curtis et al.: "Actions of Amino-Acids on the Isolated Hemisected Spinal Cord of the Toad", Brit. J. Pharmacol. (1961), 16, 262-263.
Kurokawa et al.: "The Palladium(II)-Assisted Synthesis of (±)-α-(Methylenecyclopropyl)Gylcine and (±)-Trans-α-(Carboxycyclopropyl)Glycine, Two Bioactive Amino Acids", Tetrahedron Letters, vol. 26, No. 1, pp. 83-84, 1985.
Monaghan et al.: "Anatomical Distributions of Four Pharmacologically Distinct $^3$H-L-Glutamate Binding Sites", Nature, vol. 306, 10 Nov. 1983.
Monaghan et al.: "Distribution of [$^3$H] AMPA Binding Sites in Rat Brain as Determined by Quantitative Autoradiography", Brain Research, 324 (1984) 160-164.
Ohfune et al.: "Synthesis of the Serine Equivalent, (2R) and (2S)-Amino-3-Butenol Derivatives...", Tetrahedron Letters, vol. 25, No. 10, pp. 1071-1074, 1984.
Ohfune et al.: "Synthesis of (+)-Galatinic Acid, A Constituent Amino Acid in the Peptide Antibiotic Galantin I...", Tetrahedron Letters, vol. 25, No. 15, pp. 1587-1590, 1984.
OhnHaus et al.: "Liver Blood Flow and Blood Volume Following Chronic Phenobarbitone Administration", European Journal of Pharmacology, 31 (1975) 161-165.
Shimamoto et al.: "New Routes to the Synthesis of Cis-α-(Carboxycyclopropyl)Glycines from L-- Glutamic Acid...", Tetrahedron Letters, vol. 30, No. 29, pp. 3803-3804, 1989.
Shinozaki et al.: "A Conformationally Restricted Analogue of L-Glutamate, the (2S,3R,4S)Isomer of L-α-(Carboxycyclopropyl)Glycine...", Brain Research 480 (1989) 355-359.
Watkins et al.: "Agonists and Antagonists for Excitatory Amino Acid Receptors", Tins, vol. 10, No. 7, 1987, pp. 265-272.
Yamanoi et al.: "Synthesis of Trans- and Cis-α-(Carboxycyclopropyl)Glycines", Tetrahedron Letters, vol. 29, No. 10, pp. 1181-1184, 1988.
Chemical Abstracts, vol. 110, No. 7, 13th Feb. 1989, p. 84, Abstract No. 51395e, Columbus Ohio, U.S.A.; R. Pellicciari et al.: "3,4-Cyclopropyl Glutamates as Conformationally...", Neurol. Neurobiol., 1988.
Chemical Abstracts, vol. 112, No. 11, 12th Mar. 1990, p. 93, Abstract No. 91917z, Columbus, Ohio, U.S.A.; H. Shinozaki et al., "Potent NMDA-Like Actions and Potentiation of Glutamate...", Br. J. Pharmacol., 1989, 1213-24.
Article in Tetrahedron Letters, vol. 29, No. 10, pp. 1181-1184, 1988 entitled, "Synthesis of Trans- and Cis-α-(Carboxycyclopropyl)Glycines, Novel Neuroinhibitory Amino Acids as L-Glutamate...".
Article in Tetrahedron Letters, vol. 26, No. 1, pp. 83-84, 1985 entitled, "The Palladium (II)-Assisted Syntheses of (f (+)-Trans-α-(Carboxycyclopropyl)Glycine, Two Bioactive...".

*Primary Examiner*—Michael L. Shippen
*Attorney, Agent, or Firm*—Cushman, Darby & Cushman

[57] ABSTRACT (2R,3S,4S)-α-(carboxycyclopropyl)glycine of the formula (1) and salts thereof are disclosed.

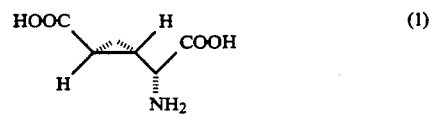

The compound (1) exhibits most potent depolarizing activities among the known NMDA agonists and will be a useful tool to investigate various neuronal functions related to the excitatory amino acid receptors.

1 Claim, No Drawings

(2R,3S,4S)-α-(CARBOXYCYCLOPROPYL)GLYCINE

The present invention relates to (2R,3S,4S)-α-(carboxycyclopropyl)glycine of the formula (1) and salts thereof.

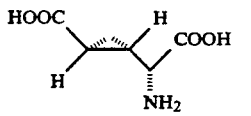

L-glutamic acid has attracted much attention because of its neurotransmitter action as well as its neuroexcitotoxic action in the mammalian central nervous system. The compound of the present invention, (2R,3S,4S)-α-(carboxycyclopropyl)glycine (1), specifically, activates the NMDA receptor which is one of the glutamate receptor subtypes. The title compound (1) exhibits most potent depolarizing activities among the known NMDA agonists. The development of this compound provides useful tool to investigate various neuronal functions related to the excitatory amino acid receptors and to design effective antagonists for various acute and chronic neurodegenerative diseases such as epilepsy and Huntington's chorea.

Elucidation of the mechanism of L-glutamic acid-receptor interaction is one of the most important subjects in life science.

The study of L-glutamate at an early stage was developed primarily through the investigation of structure-activity relationships of L-glutamate related compounds (D. R. Curtis, J. W. Phillis, J. C. Watkins, British J. Pharmacol., 16, 262-283, 1961). The discovery of excitatory actions of kainic acid and quisqualic acid has provided a variety of new opportunities for neurobiologist, i.e. the classification of glutamate receptor subtypes and the analysis of excitotoxicity in the mammalian central nervous system. At present, the glutamate receptor has been divided into at least three subtypes (J. C. Watkins, R. H. Evans, Annu. Rev. Pharmacol., 21, 165-204, 1981):

1. N-methyl-D-aspartic acid (NMDA) type
2. Kainic acid (KA) type
3. Quisqualic Acid type Thus, the study of excitatory amino acids has progressed rapidly from the identification of putative transmitters to the elucidation of their physiological functions [(a) D. T. Monaghan, V. R. Holets, D. W. Toy, C. W. Cotman, Nature, 306, 176-179, 1983; (b) D. T. Monaghan, D. Yao, C. W. Cotman, Brain Res., 324, 160-164, 1984; (c) H. J. Olvesman, D. T. Monaghan, C. W. Cotman, J. C. Watkins, Eur. Pharmac., 131, 161-162, 1986].

The physiological significance of each glutamate receptor are not always documented enough, but some diseases have been suggested to be related to the glutamate function, such as epilepsy, dyskinesia, Huntington's chorea, residual symptoms of cerebrovascular accident, and so on (B. Meldrum, ISI Atlas of Science, 228-232, 1987).

Therefore, it has been required to discover new glutamate agonists and antagonists for the treatment or the protection against these diseases. At the same time, it is very useful for the treatment of these diseases to elucidate the interaction of glutamate molecules with their receptor subtypes. In particular, it is important for the invention of new agonists or antagonists to know the interaction between the conformation of glutamate and activation of the NMDA-type receptor, because the NMDA-type receptor is thought to be directly related to neuronal loss or death induced by excitatory amino acids, which is seen after the cerebrovascular accident.

At the present time, the circumstances surrounding L-glutamic acid and its receptors as reviewed above, specifically the structure-activity relationship between L-glutamate agonists and L-glutamic acid, has not yet been made clear.

As mentioned above, the L-glutamate receptors are classified into three subtypes. It is only assumed that the structural relation between NMDA, KA and QA receptors subtype and L-glutamic acid results from the conformation of L-glutamic acid (J. C. Watkins, H. T. Olverman, Trend in Neuroscience, 10, 265-272, 1987).

On the other hand, L. Fowden et al. have isolated (2S,3S,4S)-α-(carboxycyclopropyl)glycine and (2S,3S,4R)-α-(carboxycyclopropyl)glycine from young fruits of the plant and reported that they caused hypoglycemia and amesis (L. Fowden, et al., Phytochemistry, 8, 437, 1969).

In the course of the study on the interaction of L-glutamate and receptors, the present inventors developed a method for the stereoselective synthesis of conformationally restricted glutamate analogues, namely, four isomers of carboxycyclopropyl-L-glycine which interpret the interaction between the conformation of L-glutamate and the activity of NMDA-like action. In the newborn rat spinal cord preparation, the depolarizing activity of (2S,3R,4S)-α-(carboxycyclopropyl)glycine (2), which caused a potent NMDA-type depolarization, was about 100 times more potent than that of L-glutamate (Japanese Patent Application No. 129626/88).

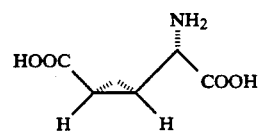

Taking the facts mentioned above into consideration, the inventors completed the invention by searching extensively for a compound which is specific to said receptor and has stronger depolarizing activity and found, surprisingly, that the D-amino acid of formula (1), that is, (2R,3S,4S)-α-(carboxycyclopropyl)glycine causes more potent depolarizing activity than the compound (2).

(2R,3S,4S)-α-(carboxycyclopropyl)glycine, the novel compound of this invention, can be prepared by the following procedure.

An ether solution of a (2R)-2-amine-3-butenol derivative of the formula (3)

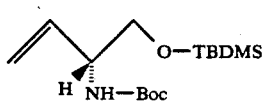

(wherein Boc is t-butoxycarbonyl; TBDMS is t-butyldimethylsilyl, the same shall apply hereinafter) is treated with ethyl diazoacetate in the presence of palladium(II) acetate to obtain four stereoisomers of (2R)-α-(carboxycyclopropyl)glycinol derivatives (4).

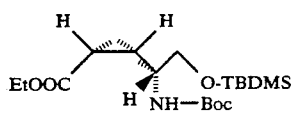

(4)

The mixture of these isomers is dissolved in ethanol and the TBDMS group is removed by treatment with an acid catalyst such as DL-camphorsulfonic acid (hereinafter abbreviated as CSA). Carboxycyclopropane derivatives of the formulae (5) and (6) can be separated by column chromatography of the produced alcohols over silica gel.

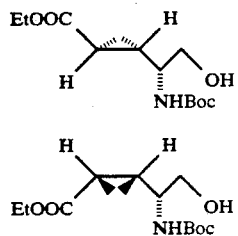

(5)

(6)

Compound (5) thus obtained is oxidized with Jones reagent and the product is deprotected to give (2R,3S,4S)-α-(carboxycyclopropyl)glycine of this invention.

In the depolarizing activity test using the spinal cord of a rat, (2R,3S,4S)-α-(carboxycyclopropyl)glycine of this invention exhibited N-methyl-D-aspartic acid (NMDA) like activity and the activity was more than 300 times as potent as that of L-glutamic acid. This activity surpasses that of NMDA and compound (2) and is the most active known at the present time.

The invention will be further illustrated by the following examples.

EXAMPLE

Palladium(II) acetate (168 mg, 0.75 mmol) was dissolved in an ether solution (50 ml) of t-butyldimethylsilyl ether of (2R)-N-t-butoxycarbonyl-2-amino-3-butenol (3) (4.34 g, 15.0 mmol) and to this was added an ether solution (100 ml) of ethyl diazoacetate (17.1 g, 150 mmol) and palladium(II) acetate (168 mg, 0.75 mmol) over 3 hours. The insoluble material in the reaction mixture was filtered off and the filtrate was concentrated under reduced pressure to give an oily product. Purification of the product by column chromatography over silica gel (20% ether/hexane) afforded t-butyldimethylsilyl ether of (2R)-N-t-butoxycarbonyl-2-(ethoxycarbonylcyclopropyl)glycinol (4) as an oil (4.00 g, 87.9%). Compound (4) thus obtained was dissolved in ethanol (70 ml) and CSA (10 mg) was added to this solution then the mixture was stirred for 16 hours at room temperature. The solvent was removed under reduced pressure and the residue was subjected to medium pressure column chromatography over silica gel (50% ether/hexane) 932 mg of (2R,3S,4S)-N-t-butoxycarbonyl-2-(ethoxycarbonylcyclopropyl)glycinol (5), 175 mg of its stereoisomer (6) and 560 mg of a mixture of inseparable stereoisomer.

(2R,3S,4S) isomer (5)
colorless needles, m.p. 89.0°-89.5° C. $[\alpha]_D^{25} + 47.4°$ (C 1.02, CHCl$_3$) $^1$H-NMR (360 MHz, CDCl$_3$ δ ppm): 1.03(1H,m), 1.17(1H,m), 1.25(3H,t,J=7 Hz), 1.44(9H,s), 1.57(2H,m), 2.74(1H,s), 3.22(1H,m), 3.60-3.77(2H,m), 4.11(2H,dq,J=7, 14 Hz), 4.96(1H,d,J=8 Hz)

IR (film, ν, cm$^{-1}$): 3460, 3028, 1712

(2R,3R,4S) isomer (6)
colorless needles, m.p. 94.5°-95.0° C. $[\alpha]_D^{25} + 50.9°$ (C 0.98, CHCl$_3$) $^1$H-NMR (360 MHz, CDCl$_3$ δ ppm): 1.15(2H,m), 1.27(3H,t,J=7 Hz), 1.53(1H,m), 1.77(1H,m), 3.02(1H,bs), 3.61(1H,m), 3.65-3.90(2H,m), 4.15(2H,dq,J=7, 14 Hz), 4.95(1H,s)

IR (film, ν, cm$^{-1}$): 3392, 2984, 1716

To a solution of compound (5) (500 mg, 1.83 mmol) in acetone (20 ml) was added Jones reagent at 0° C. and the mixture was stirred for 3 hours at the same temperature. Stirring was continued for further 1.5 hours at room temperature and then isopropyl alcohol was added to quench the excess reagent. After the addition of aqueous sodium bicarbonate, the mixture was washed with ether to remove the unreacted starting material and the pH of the aqueous layer was adjusted to 2 with citric acid. Then the resulting mixture was extracted with ethyl acetate. The organic layer was washed with water, dried over magnesium sulfate, evaporated under reduced pressure and the residue was again dissolved in tetrahydrofurane (3 ml). 0.5N sodium hydroxide (3.5 ml) was added to this solution at 0° C. and the mixture was stirred for 19 hours. The pH of the reaction mixture was adjusted to 2 with 1N hydrochloric acid and after the addition of aqueous saturated sodium chloride the mixture was extracted with ethyl acetate. The organic layer was dried over magnesium sulfate and the solvent was removed under reduced pressure to give N-t-butoxycarbonyl-α-(carboxycyclopropyl)glycine (420 mg, 88.5%). This product was dissolved in methylenechloride (2 ml) and trifluoroacetic acid (2 ml) was added to this solution at 0° C. After being stirred for 30 minutes the reaction mixture was concentrated under reduced pressure and the residue was subjected to ion exchange column chromatography over Dowex 50 W×4. After the column was washed with water the desired compound was eluted with 1N ammonia water and it was obtained as an ammonia salt. This salt was dissolved in water and the pH was adjusted to 3 with 1N hydrochloric acid. The resulting crystals were filtered off and recrystallized from water to give the compound of this invention as white crystals (80 mg).

m.p. 254°-258° C. (decomp.) $^1$H-NMR (360 MHz, D$_2$O, δ ppm): 1.15(1H,m), 1.32(1H,m), 1.76(1H,m), 1.95(1H,m), 3.40(1H,d,J=9.0 Hz)

$[\alpha]_D^{25} + 21.6°$ (C 0.50, H$_2$O)

Pharmacological Test

The methods used for the electrophysiological experiment in the isolated newborn rat spiral cord were essentially similar to those described by Ohtsuka et al. (Nature, 252, 733-734, 1974). The potential changes generated in the motoneurones induced by L-glutamate analogues, namely, (2R,3S,4S)-α-(carboxycyclopropyl)glycine (1) of this invention and one of the stereoisomers, (2S,3R,4S)-α-(carboxycyclopropyl)-glycine (2) were recorded extracellularly from the ventral root with a suction electrode. The experimental results are summarized in Table 1.

TABLE 1

| Compound | Minimum effective concentration mol/l | relative activity |
|---|---|---|
| L-Glu*[1] | 1 × 10$^{-4}$ | 1 |
| (1) | 3 × 10$^{-7}$*[2] | 300 |

TABLE 1-continued

| Compound | Minimum effective concentration mol/l | relative activity |
| --- | --- | --- |
| (2) | $1 \times 10^{-6}$*2 | 100 |

*1 L-glutamic acid
*2 The activity disappeared when measured in the presence of 2-APV or Mg++.

Glutamate receptors in the mammalian central nervous system have been classified into the three subtypes, namely, 1) NMDA type, 2) KA type and 3) QA type. Compound (1) of this invention is thought to interact with the NMDA type receptor since activity disappears in the presence of 2-APV or Mg++. Furthermore, the activity of (1), as shown in Table 1, is 300 times as potent as L-glutamic acid, 3 times as potent as compound (2) which has already been put forward for a patent, and much more potent than NMDA.

The above results indicate that compound (1) will be useful as a tool to investigate various neuronal functions.

What is claimed is:

1. (2R,3S,4S)-α-(carboxycyclopropyl)glycine of the formula (1) or salts thereof selected from the group consisting of ammonium, sodium, potassium and calcium salts.

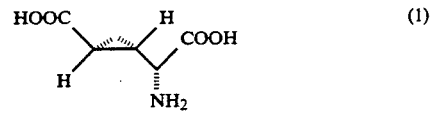

(1)

* * * * *